United States Patent [19]

McCain et al.

[11] Patent Number: 5,112,789
[45] Date of Patent: May 12, 1992

[54] ALKOXYLATION CATALYSIS

[75] Inventors: James H. McCain, Charleston; Stephen W. King, Scott Depot; Robert J. Knopf, St. Albans; Charles A. Smith, South Charleston; Charles F. Hauser, Charleston, all of W. Va.

[73] Assignee: Union Carbide Chemicals & Plastics Technology Corporation, Danbury, Conn.

[21] Appl. No.: 251,431

[22] Filed: Sep. 30, 1988

[51] Int. Cl.$^5$ .............................................. B01J 31/00
[52] U.S. Cl. ...................... 502/162; 502/167; 502/168; 502/170; 502/171; 502/172
[58] Field of Search ............... 502/162, 167, 168, 170, 502/171, 172

[56] References Cited

U.S. PATENT DOCUMENTS

| | | | |
|---|---|---|---|
| 2,934,505 | 4/1960 | Gurgiolo | 260/2 |
| 3,328,306 | 6/1967 | Ellis | 252/90 |
| 3,432,445 | 3/1969 | Oagan et al. | 260/2 |
| 3,607,785 | 9/1971 | Oagan et al. | 252/431 C |
| 3,682,849 | 8/1972 | Smith et al. | 260/615 B |
| 4,098,818 | 7/1978 | Krummel et al. | 260/535 R |
| 4,112,231 | 9/1978 | Weibull et al. | 544/174 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,281,087 | 7/1981 | Heuschen et al. | 525/361 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,326,047 | 4/1982 | Yates | 525/507 |
| 4,359,589 | 11/1982 | Brownscombe | 568/618 |
| 4,360,698 | 11/1982 | Sedan | 568/618 |
| 4,375,564 | 3/1983 | Edwards | 568/618 |
| 4,396,779 | 8/1983 | Edwards | 568/618 |
| 4,396,780 | 8/1983 | Shtykh et al. | 568/620 |
| 4,453,022 | 6/1984 | McCain et al. | 568/618 |
| 4,453,023 | 6/1984 | McCain et al. | 568/618 |
| 4,465,877 | 8/1984 | Edwards | 568/618 |
| 4,472,560 | 9/1984 | Kuyper et al. | 526/120 |
| 4,474,678 | 10/1984 | Lutz et al. | 252/174.21 |
| 4,477,589 | 10/1984 | van der Hulst et al. | 502/169 |
| 4,490,561 | 12/1984 | Yang et al. | 568/615 |
| 4,568,774 | 2/1986 | Yang | 568/616 |
| 4,654,417 | 3/1987 | Inoue et al. | 528/416 |
| 4,659,778 | 4/1987 | Williams | 525/107 |
| 4,665,236 | 5/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |
| 4,754,075 | 6/1988 | Knopf et al. | 568/618 |
| 4,775,653 | 10/1988 | Leach et al. | 502/170 |
| 4,892,977 | 1/1990 | Nieh | 568/618 |

FOREIGN PATENT DOCUMENTS

| | | |
|---|---|---|
| 0026544 | 4/1981 | European Pat. Off. . |
| 0026546 | 4/1981 | European Pat. Off. . |
| 0026547 | 4/1981 | European Pat. Off. . |
| 0033359 | 6/1981 | European Pat. Off. . |
| 0082569 | 6/1983 | European Pat. Off. . |
| 0085167 | 6/1983 | European Pat. Off. . |
| 0095562 | 12/1983 | European Pat. Off. . |
| 0104309 | 4/1984 | European Pat. Off. . |
| 0180266 | 5/1986 | European Pat. Off. . |
| 0180267 | 5/1986 | European Pat. Off. . |
| 0212820 | 3/1987 | European Pat. Off. . |
| 0228121 | 7/1987 | European Pat. Off. . |
| 0273521 | 7/1988 | European Pat. Off. . |
| 1462133 | 1/1977 | United Kingdom . |
| 1462134 | 1/1977 | United Kingdom . |
| 1399966 | 7/1985 | United Kingdom . |

OTHER PUBLICATIONS

Kochurovskaya, G. G. et al., Kriobiol. Kriomed., 3, 1977, pp. 76–79.
Turova, N. Y. et al., Chemical Reviews-Uspekhi Khimii, Mar. 1965, pp. 161–185.
U.S. patent application Ser. No. 186,937, filed Apr. 27, 1988 (D-1255-1).
U.S. patent application Ser. No. 186,938, filed Apr. 27, 1988 (D-12337).
Schick, M. J., Nonionic Surfactants, vol. 1, Marcel Dekker, Inc., New York, N.Y. (1967) pp. 28–41.
U.S. patent application Ser. No. 454,560, filed Dec. 30, 1982 (D-13322).
U.S. patent application Ser. No. 102,939, filed Sep. 30, 1987, (D-15778).

Primary Examiner—Patrick P. Garvin
Assistant Examiner—E. D. Irzinski
Attorney, Agent, or Firm—Rose M. Allen

[57] ABSTRACT

This invention relates to modified bimetallic or polymetallic (other than Groups IA, IIA and IIB metals) catalysts and the use thereof in the preparation of alkoxylation products, i.e., condensation reaction products of alkylene oxides and organic compounds having at least one active hydrogen. In another aspect of this invention, processes are provided for preparing the modified bimetallic or polymetallic catalysts for alkoxylation using a divalent or polyvalent metal or a divalent or polyvalent metal-containing compound as sources for the catalytically-active metal. In a further aspect of this invention, processes are provided for preparing alkoxylation products that have beneficial, narrow molecular weight ranges using the modified bimetallic or polymetallic catalysts.

26 Claims, No Drawings

ALKOXYLATION CATALYSIS

RELATED APPLICATIONS

The following are related, commonly assigned applications, filed on an even date herewith:

U.S. patent application Ser. No. 251,430, now U.S. Pat. No. 4,946,984; U.S. patent application Ser. Nos. 251,434; 251,433; 251,436; and 251,432.

BRIEF SUMMARY OF THE INVENTION

1. Technical Field

This invention relates to modified bimetallic or polymetallic (other than Groups IA, IIA and IIIB metals) catalysts and the use thereof in the preparation of alkoxylation products, i.e., condensation reaction products of alkylene oxides and organic compounds having at least one active hydrogen. In another aspect of the invention, processes are provided for preparing the modified bimetallic or polymetallic catalysts for alkoxylation using a divalent or polyvalent metal or a divalent or polyvalent metal-containing compound, e.g., aluminum isopropoxide, as sources for the catalytically-active metal. In a further aspect of the invention, processes are provided for preparing alkoxylation products that have beneficial, narrow molecular weight ranges using the modified bimetallic or polymetallic catalysts.

2. Background of the Invention

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a greater portion of water is usually required otherwise gelling may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products.

One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
|---|---|---|
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation Distribution, % | 3.8 | 2.54 |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published Dec. 12, 1983, exemplifies the ability to obtain high selectivity to low ethoxylate species when low ratios of ethylene oxide reactant to alcohol are employed as well as the tendency to rapidly lose that selectivity when higher ethoxylated products are sought. For instance, Example 1, (described as a 1 mole EO adduct), which reports the use of a diethylaluminum fluoride catlyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
|---|---|---|
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Recently, Yang and coworkers were granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093.

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European patent publication No. 0026544, No. 0026547, and No. 0026546, all herein incorporated by reference. These workers have also disclosed the use of strong acids to partially neutralize and thereby promote the catalytic action of certain alkaline earth metal derivatives. See U.S. Pat. Nos. 4,453,022 and 4,453,023 (barium-containing catalyst), both herein incorporated by reference.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 18 weight percent of the composition and alkoxylation products having more than three alkoxyl groups than the average peak alkoxylation component comprise very little of the product mixture.

U.S. Pat. Nos. 4,754,075, 4,886,917 and 4,820,673, herein incorporated by reference, relates to processes for preparing alkoxylation mixtures having relatively narrow alkoxylation product distributions using modified, calcium-containing catalysts. Processes are also disclosed for making alkoxylation catalysts using calcium oxide and/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

U.S. Pat. No. 4,902,658, herein incorporated by reference, relates to heterogeneous (organic polymer-supported) calcium-containing catalysts and the use thereof in the preparation of alkoxylation products, i.e., condensation reaction products of alkylene oxides and organic compounds having at least one active hydrogen. Processes are provided for preparing heterogeneous (organic polymer-supported) calcium-containing catalysts for alkoxylation using calcium oxide or calcium hydroxide as sources for the catalytically-active calcium. Alkoxylation products are provided that have beneficial, narrow molecular weight ranges and are essentially neutral in pH and free from catalyst residues.

DISCLOSURE OF THE INVENTION

This invention relates to modified bimetallic and polymetallic (other than Groups IA, IIA and IIIB metals) alkoxylation catalysts and to processes for making the catalysts using a divalent or polyvalent metal or a divalent or polyvalent metal-containing compound, e.g., aluminum isoproxide, as sources for the catalytically-active metal. This invention further relates to processes for preparing alkoxylation product mixtures having relatively narrow alkoxylation product distributions using the modified bimetallic and polymetallic catalysts. As used herein, Group IA metals shall include lithium, sodium, potassium, rubidium, cesium and francium. Also, as used herein, Group IIA metals shall include beryllium, magnesium, calcium, strontium, barium and radium. Further, as used herein, Group IIIB metals shall include scandium, yttrium, lanthanum, cerium, praseodymium, neodymium, promethium, samarium, europium, gadolinium, terbium, dysprosium, holmium, erbium, thulium, ytterbium, lutetium, thorium, protactinium, uranium and plutonium.

The modified bimetallic and polymetallic catalysts of this invention are modified with an organic or inorganic oxyacid having a divalent or polyvalent anion such as sulfuric acid, phosphoric acid, carbonic acid, pyrosulfuric acid and the like, or by a divalent or polyvalent metal salt of an organic or inorganic oxyacid such as aluminum sulfate, zinc sulfate, zinc phosphate and the like. Mixtures of divalent or polyvalent oxyacids, e.g., sulfuric acid and phosphoric acid, mixtures of divalent or polyvalent metal salts of oxyacids, e.g., aluminum sulfate and zinc phosphate, and mixtures of divalent or polyvalent oxyacids and divalent or polyvalent metal salts of oxyacids, e.g., sulfuric acid and zinc phosphate, can be used in the processes of this invention. The divalent or polyvalent oxyacids and the divalent or polyvalent metal salts of oxyacids are at times referred to hereinafter as "modifiers". These modified catalysts are believed to have complex structures which are probably comprised of a mixture of species, certain of which may not even be catalytically active. Those species which are catalytically active are believed to have structures of the type depicted by the following formula:

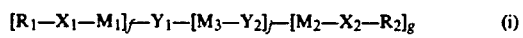

wherein:

R$_1$ and R$_2$ are independently hydrogen or an organic residue of an organic compound having at least one active hydrogen;

X$_1$ and X$_2$ are independently oxygen, sulfur or nitrogen;

$M_1$, $M_2$ and $M_3$ are independently a divalent or polyvalent metal other than a Group IIA or IIIB metal;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum f+g is equal to the valence of $Y_1$ when j is a value of 0, and f and g are integers having a value such that the sum f+g is equal to the valence of $Y_1$ plus $[M_3-Y_2]_j$ when j is a value other than 0. It is understood that formula (i) is speculation only. As used herein, divalent shall mean a valence of 2 and polyvalent shall mean a valence of more than 2. Also, as used herein, bimetallic shall mean 2 metals which can be the same or different and polymetallic shall mean more than 2 metals which can be the same or different.

For purposes of this invention including the claims hereinafter, it is understood that formula (i) shall be inclusive of polyvalency requirements for $M_1$, $M_2$ and $M_3$ and that such polyvalency requirements are appropriately satisfied in formula (i). It is also understood that any polyvalency requirements of $M_3$ may be satisfied by $R_1-X_1-$ or $R_2-X_2-$.

Another aspect of the invention provides a method for preparing a modified bimetallic or polymetallic alkoxylation catalyst, which method comprises (i) reacting or solubilizing, at least in part, a first divalent or polyvalent metal other than a Group IIA or IIIB metal or a first divalent or polyvalent metal-containing compound, e.g., aluminum isopropoxide, other than a Group IIA or IIIB metal-containing compound, by mixing with an activator or an organic compound having at least one active hydrogen to form a first divalent or polyvalent metal-containing composition, (ii) reacting a second divalent or polyvalent metal other than a Group IIA or IIIB metal or a second divalent or polyvalent metal-containing compound other than a Group IIA or IIIB metal-containing compound with an organic compound having at least one active hydrogen to produce a second divalent or polyvalent metal-containing composition, (iii) reacting the first divalent or polyvalent metal-containing composition with the second divalent or polyvalent metal-containing composition under effective reaction conditions to produce a catalyst precursor composition, and (iv) reacting the catalyst precursor composition with an oxyacid having a divalent or polyvalent anion or a divalent or polyvalent metal salt of an oxyacid or mixtures thereof under effective reaction conditions to produce the alkoxylation catalyst. Steps (i) and (ii) may be carried out concurrently using the same reaction equipment. The term "solubilizing" as used herein is intended to mean that the divalent or polyvalent metal is provided in an active form; however, the term is not intended to be limiting to the formation of a truly dissolved divalent or polyvalent metal specie (which may or may not exist).

The solubilization may be effected by mixing certain divalent or polyvalent metal-containing compounds, for example, with an organic compound having at least one active hydrogen or an activator having the general formula $Z_a-X-Q-Y-Z'_b$ wherein X and Y are the same or different electronegative (relative to carbon), hetero (i.e., non-carbon) atoms selected from the group consisting of oxygen, nitrogen, sulfur and phosphorous; a and b are the same or different integers satisfying the valency requirements of X and Y; Q is any organic radical which is electropositive or essentially neutral relative to X and/or Y, which does not prevent the solubilization, and which contains at least one carbon atom and preferably has the formula:

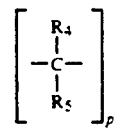

wherein $R_4$ and $R_5$ are the same or different and are selected from the group consisting of hydrogen and lower alkyl or alkylene groups of one to four carbon atoms, and p is an integer from 1 to 6, preferably 2 to 4; Z and Z' are the same or different and are either hydrogen or an organic radical which does not interfere with the function of the activator for its intended purpose, i.e., its solubilizing and/or stabilizing function, thereby forming the first divalent or polyvalent metal-containing composition which is then reacted with the second divalent or polyvalent metal-containing composition to produce the catalyst precursor composition. The catalyst precursor composition is then reacted with the divalent or polyvalent oxyacid or the divalent or polyvalent metal salt of the oxyacid to produce a catalyst which is catalytically active in the alkoxylation of compounds having active hydrogens, especially alcohols.

The modified bimetallic or polymetallic catalyst composition can be directly contacted with alkylene oxides to form alkoxylates of the organic compound employed having an active hydrogen, to produce alkoxylates. If an activator is used which does not have an active hydrogen, excess activator should preferably be removed prior to alkoxylation.

According to further embodiments of this aspect of the invention, an exchange reaction is carried out either prior to or after the reaction of the catalyst precursor composition with the oxyacid having a divalent or polyvalent anion or the divalent or polyvalent metal salt of an oxyacid under conditions at which an exchange reaction will occur, with at least one organic compound having an active hydrogen, e.g., an alcohol, having a higher boiling point (and usually a longer carbon chain length) than said organic compound employed to form the corresponding, catalytically active higher boiling derivative of the catalyst precursor composition. This latter catalytic species can then be directly contacted with alkylene oxide to form alkoxylates of the higher boiling material.

The alkoxylation processes of this invention involve the condensation reaction of an alkylene oxide and at least one organic compound having at least one active hydrogen in the presence of a catalytically effective amount of a modified bimetallic or polymetallic catalyst as described above. The modifier is employed in an amount of about 0.2 to 0.9, e.g., 0.35 to 0.85, often, about 0.45 to 0.75, times that required to give a normal equivalence of metal to anion, which is sufficient to narrow the distribution of the alkoxylation product mixture and provide at least one alkoxylation specie in an amount of at least about 18 weight percent of the mixture. The modified bimetallic or polymetallic catalyst is prepared under sufficient agitation to ensure a relatively uniform product. A useful oxyacid anion is the phosphoric acid anion.

By this invention, alkoxylation product mixtures are provided which have a narrow, but balanced distribution of alkoxylation species. These product mixtures are relatively free from large amounts of substantially higher alkoxylation moieties, i.e. those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species.

The alkoxylation product mixtures prepared by the processes of this invention are characterized as the condensation reaction products of alkylene oxides and organic compounds having at least one active hydrogen in which the mole ratio of reacted alkylene oxide per active hydrogen is at least about 4, say, about 4 to 16 or 24, preferably about 5 to 12. The product mixtures have at least one alkoxylation moiety which constitutes at least about 18, say, about 20 to 30 or 40, and most often about 20 to 30, weight percent of the composition. The alkoxylation mixtures of this invention also have a relatively symmetrical distribution. Hence, the Portion of the product mixture having three or more oxyalkylene unit groups (per active hydrogen site of the organic compound) than the peak alkoxylation species is relatively minor, e.g., often less than about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation species is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation species are present in a weight ratio to the most prevalent alkoxylation specie of about 0.6:1 to 1:1.

The preferred alkoxylation product mixtures of this invention correspond to the formula $$P_n = A \times e^{-(n-\bar{n})^2/(2.6 + 0.4\bar{n})}$$

wherein n is the number of oxyalkylene groups per reactive hydrogen site for an alkoxylation species (n must equal at least one) of the composition, $\bar{n}$ is the weight average oxyalkylene number, A is the weight percent of the most prevalent alkoxylation specie in the mixture and $P_n$ is, within plus or minus two percentage points, the weight percent of the alkoxylation specie having n oxyalkylene groups (per active hydrogen site) in the mixture. This distribution relationship generally applies where n is between the amount of $\bar{n}$ minus 4 to the amount of $\bar{n}$ plus 4.

For purposes herein, the average peak alkoxylation specie is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture (including unreacted alcohol), i.e., $\bar{n}$ equals the sum of $(n)(P_n)$ for all the species present divided by 100.

Preferred alkoxylation product mixtures of this invention include poly(oxyethylene)glycols, i.e., CARBOWAX® and fatty alcohol ethoxylates, i.e., TERGITOL®. CARBOWAX® is the registered trademark of Union Carbide Corporation for a series of poly(oxyethylene)glycols. Ethylene glycol can be used to make the CARBOWAX® poly(oxyethylene)glycols or the CARBOWAX® poly(oxyethylene)glycols can be used to make higher molecular weight CARBOWAX® poly(oxyethylene)glycols. For example, CARBOWAX® poly(oxyethylene)glycol 200 can be used to make CARBOWAX® poly(oxyethylene)glycol 400. Specifically, the CARBOWAX® poly(oxyethylene)glycols are liquid and solid polymers of the general formula $H(OCH_2CH_2)_wOH$, where w is greater than or equal to 4. In general, each CARBOWAX® poly(oxyethylene)glycol is followed by a number which corresponds to its average molecular weight. Examples of useful CARBOWAX® poly(oxyethylene)glycols are: CARBOWAX® poly(oxyethylene)glycol 200, which has an average w value of 4 and a molecular weight range of 190 to 210; CARBOWAX® poly(oxyethylene)glycol 400, which has an average w value between 8.2 and 9.1 and a molecular weight range of 380 to 420; and CARBOWAX® poly(oxyethylene)glycol 600, which has an average w value between 12.5 and 13.9 and a molecular weight range of 570 to 630.

TERGITOL® is the registered trademark of Union Carbide Corporation for a series of ethoxylated nonylphenols, primary and secondary alcohols, i.e., nonionic surfactants, and the sodium salts of the acid sulfate of secondary alcohols of 10 to 20 carbon atoms, i.e., anionic surfactants. Examples of the TERGITOL® nonionic surfactants include TERGITOL® S Nonionics which have the general formula $CH_3(CH_2)_xCH(CH_3)-O-(CH_2CH_2O)_yH$ wherein x is a value of 9-11 and y is a value of about greater than 1. Examples of the TERGITOL® anionic surfactants include TERGITOL® Anionic 08, which is $C_4H_9CH(C_2H_5)CH_2SO_4-Na$; TERGITOL® Anionic 4, which is $C_4H_9CH(C_2H_5)C_2H_4CH-(SO_4Na)CH_2CH(CH_3)_2$; and TERGITOL® Anionic 7, which is $C_4H_9CH(C_2H_5)C_2H_4CH-(SO_4Na)C_2H_4CH(C_2H_5)_2$.

DETAILED DESCRIPTION

As indicated above, the modified bimetallic or polymetallic catalysts of this invention are modified with an organic or inorganic oxyacid having a divalent or polyvalent anion such as sulfuric acid, phosphoric acid, carbonic acid, pyrosulfuric acid and the like, or by metal salts of organic or inorganic oxyacids having divalent or polyvalent anions such as aluminum sulfate, zinc sulfate, zinc phosphate and the like or mixtures thereof. These modified catalysts are believed to have complex structures which are probably comprised of a mixture of species, certain of which may not even be catalytically active. Those species which are catalytically active are believed to have structures of the type depicted by the following formula:

$$[R_1-X_1-M_1]_f-Y_1-[M_3-Y_2]_f-[M_2-X_2-R_2]_g \qquad (i)$$

wherein:

$R_1$ and $R_2$ are independently hydrogen or an organic residue of an organic compound having at least one active hydrogen;

$X_1$ and $X_2$ are independently oxygen, sulfur or nitrogen;

$M_1$, $M_2$ and $M_3$ are independently a divalent or polyvalent metal other than a Group IIA or IIIB metal;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum f+g is equal to the valence of $Y_1$ when j is a value of 0, and f and g are integers having a value such that the sum f+g is equal to the valence of $Y_1$ plus $[M_3-Y_2]_j$ when j is a value other than 0. It is understood that formula (i) is speculation only.

The alkoxylation product mixtures of this invention are enabled by the use of modified bimetallic or polymetallic catalysts that have been modified by strong, divalent or polyvalent oxyacids or divalent or polyvalent metal salts of strong oxyacids or mixtures thereof sufficient to provide a defined narrow distribution of alkoxylation products. The alkoxylation conditions may otherwise vary while still obtaining a narrower distribution of alkoxylate products.

The modifier of the catalyst is a divalent or polyvalent acid or a divalent or polyvalent metal salt of an oxyacid or mixtures thereof and contains at least one, most often at least about 2, oxygen atoms that are conventionally depicted as double bonded to the nucleus atom. Such acids and metal salts include, for example, sulfuric and phosphoric acid and the sulfates and phosphates of zirconium, zinc and aluminum; in general, desired narrow distributions are obtained using phosphoric acid and the metal phosphates.

The types of divalent and polyvalent anions of oxyacids and metal salts of oxyacids suitable for use in this invention, e.g., $Y_1$ and $Y_2$, include by way of example only, sulfates, e.g., $SO_4^{-2}$, phosphates, e.g., $PO_4^{-3}$, manganates, e.g., $MnO_4^{-2}$, titanates, e.g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates and the like.

Illustrative of metals which may be included in the divalent or polyvalent metal salt modifier and also in the divalent or polyvalent metal-containing compositions described hereinafter include titanium, zirconium, hafnium, vanadium, niobium, tantalum, chromium, molybdenum, tungsten, manganese, iron, cobalt, nickel, copper, zinc, cadmium, mercury, boron, aluminum, gallium, indium, thallium, carbon, silicon, germanium, tin, lead, phosphorus, arsenic, antimony, sulfur, selenium and tellurium.

The amount of modifier employed and the manner in which it is introduced to prepare the catalyst can be determinative of whether the desired narrow distribution with at least one alkoxylation specie being present in an amount of at least about 18 weight percent of the composition, is achieved. While not wishing to be limited to theory, it is believed that active catalysts for producing narrow distributions of alkoxylation products comprise a divalent or polyvalent metal atom (other than a Group IIA or IIIB metal atom) and another divalent or polyvalent metal atom(s) other than a Group IIA or IIIB metal atom in association with the modifier anion in a manner in which the divalent or polyvalent metal atom(s) are activated as illustrated for formula (i) hereinabove. The amount of modifier added is in an amount of about 0.2 to 0.9, say, about 0.45 to 0.75, times that required to give a normal equivalence of metal to anion.

In general, at the time of modification, the catalyst precursor composition may be represented by the following formula:

$$[R_1-X_1-M_1]_f-X_3-[M_3-X_4]-[M_2-X_2-R_2]_g \quad (ii)$$

wherein $R_1$, $R_2$, $X_1$, $X_2$, $M_1$, $M_2$, $M_3$, j, f and g are as defined hereinabove and $X_3$ and $X_4$ are independently oxygen, sulfur or nitrogen. $R_1$ and $R_2$ independently may also contain double bonded oxygen (the organic compound was a carboxylic acid), heteroatom such as oxygen, sulfur, nitrogen and phosphorous (e.g., the organic compound was a glycol, polyamine, ether of a glycol or the like). Frequently, $R_1$ and $R_2$ may comprise 1 to 20 carbons. It is understood that formula (ii) is speculation only.

For purposes of this invention including the claims hereinafter, it is understood that formula (ii) shall be inclusive of polyvalency requirements for $M_1$, $M_2$ and $M_3$ and that such polyvalency requirements are appropriately satisfied in formula (ii). It is also understood that any polyvalency requirements of $M_3$ may be satisfied by $R_1-X_1-$ or $R_2-X_2-$.

The modifier appears to enable the desired catalytically active modified metal-containing species to form; however, it has been found that depending upon other conditions during the modification, different amounts of modifier will provide the optimum catalyst in terms of selectivity and reaction rate during an alkoxylation process. Accordingly, an aspect of the invention is providing a level of modification sufficient to achieve the narrow distribution of alkoxylate product mixtures.

The medium containing the modified bimetallic or polymetallic catalyst can also affect whether the resulting modified bimetallic or polymetallic catalyst enables the desired narrow distribution of alkoxylation products to be formed. If the medium comprises as the predominant component, i.e., solvent, a material that has a low dielectric constant, the modifier can form a separate liquid phase and increased difficulty in obtaining an intimate admixture may be observed. On the other hand, with solvents that are too polar, the organic moiety in association with the divalent or polyvalent metal atom(s) may be displaced with the solvent. Most often, the medium and the organic compound providing the moiety on the divalent or polyvalent metal atom(s) are the same. Particularly convenient media include ethylene glycol, propylene glycol, diethylene glycol, glycerol, butanediols, 1,3-propanediol, and the like. Conveniently, the medium employed, if not intended to be a reactant for producing alkoxylates, should have a sufficiently low boiling point that can readily be removed from the catalyst and organic compound reactant mixture by distillation. In some instances, the medium comprises a solvent having at least two heteroatoms such as the activators described herein.

The modifier is preferably added while the catalyst precursor composition is being vigorously agitated. In this regard, a slow addition of the modifier to the catalyst precursor composition is preferred. Generally, less than 10 percent of the modifier to be added is added to the catalyst precursor composition at any one time. The addition of the modifier can be conducted at a convenient temperature, e.g., about 10° C. to 160° C., say, about 50° C. to 150° C. Preferably, a nitrogen atmosphere is advantageous. It may be advantageous to introduce the modifier in aqueous form.

The bimetallic or polymetallic catalyst having substituents of the formulae $R_1X_1-$ and $-X_2R_2$ may be prepared in any suitable manner. For example, a first divalent or polyvalent metal-containing composition can be prepared by reacting a divalent or polyvalent metal other than a Group IIA or IIIB metal or a divalent or polyvalent metal-containing compound other than a Group IIA or IIIB metal-containing compound such as aluminum isopropoxide or other suitable sources of divalent or polyvalent metals described below with an organic compound containing an active hydrogen atom of the formula $R_1X_1H$ or $HX_2R_2$. A second divalent or polyvalent metal-containing composition other than a Group IIA or IIIB metal-containing composition can be prepared by reacting a divalent or polyvalent metal described hereinabove or other suitable source of divalent or polyvalent metal with an organic compound containing an active hydrogen atom of the formula $R_1X_1H$ or $HX_2R_2$. The first divalent or polyvalent metal-containing composition and the second divalent or polyvalent metal-containing composition are then reacted under effective reaction conditions to produce a catalyst precursor composition. With compounds having higher molecular weights, e.g., 4 or more carbons, it may be generally preferred to use a lower molecular weight and more reactive and volatile compound of the formulae $R_1X_1H$ or $HX_2R_2$ (e.g., of 1 to about 3 carbons, especially compounds such as ethanol, ethylamine, ethylene glycol and the like) and then exchange that substituent with the higher molecular weight substituent while removing the lower molecular weight material by volatilization. The catalyst precursor composition is then reacted with a divalent or polyvalent oxyacid or a divalent or polyvalent metal salt of an oxyacid to produce the modified bimetallic or polymetallic alkoxylation catalyst.

The compounds having the formulae $R_1X_1H$ and $HX_2R_2$ include those organic compounds having active hydrogens described in connection with the alkoxylation products of this invention, such as alcohols, phenols, carboxylic acids and amines. Most often, the compounds having the formulae $R_1X_1H$ and $HX_2R_2$ are alcohols. When an exchange reaction is to be conducted to provide a higher molecular weight substituent on the divalent or polyvalent metal atom(s), it is generally preferred to conduct the modification prior to exchange and use a lower molecular weight material for the replacement substituent to enhance the modification process. Suitable organic compounds having active hydrogens for use in this invention include the products of hydroformylation/hydrogenation reactions.

Illustrative of first divalent or polyvalent metal-containing compounds/compositions for use in this invention include soluble metal-containing compounds/compositions per se or metal-containing compounds/compositions which can be converted to a soluble form upon interaction with the alkoxylation process reactants, e.g., activator. Examples of specific first divalent or polyvalent metal-containing compounds/compositions include one or more reaction products of divalent or polyvalent metals other than Group IIA and IIIB metals with various alcohols (alcoholates such as metal alkoxides and phenoxides) as well as oxide, hydroxide, ammoniate, amide, thiolate, carbide, thiophenoxide, nitride, thiocyanate and carboxylate compounds, e.g., acetates, formates, oxalates, citrates, benzoates, laurates and stearates. The preferred first divalent or polyvalent metal-containing compounds are aluminum-containing compounds or mixtures thereof, and the preferred first divalent or polyvalent metal-containing compositions are aluminum alcoholates.

The preparation of the modified bimetallic or polymetallic catalyst composition from a first divalent or polyvalent metal or a first divalent or polyvalent metal-containing compound as described herein and a second divalent or polyvalent metal or suitable source of the divalent or polyvalent metal as described herein is typically conducted at elevated temperatures, e.g., from about 30° C. to 200° C. or more, and in a liquid medium. The organic compound which provides the substitution is normally provided in excess of that required for reaction with the divalent or polyvalent metal-containing reactant(s). Hence, the weight ratio of divalent or polyvalent metal-containing reactant(s) to the organic compound frequently is within the range of about 0.01:100 to 25:100. The reaction may, if desired, be conducted in the presence of an inert liquid solvent. The exchange reaction is also conducted under elevated temperature and, optionally, under reduced pressure to facilitate removal of the more volatile components. Temperatures may range from about 50° C. to 250° C., say, about 80° C. to 200° C. or 250° C., and pressures (absolute) are often in the range of 1 millibar to 5 bars, e.g., about 10 millibars to 2 bars.

It is usually desired that the organic substituent on the modified bimetallic or polymetallic catalyst composition correspond to the "starter" component for the alkoxylation process. The starter component is the organic compound having at least one active hydrogen with which the alkylene oxide reacts.

The alkoxylation is conducted using a catalytically-effective amount of the modified bimetallic or polymetallic catalyst, e.g., about 0.001 to 10, often about 0.5 to 5, weight percent based on the weight of the starter component. The catalysts substantially retain their activities during the alkoxylation, regardless of the amount of alkylene oxide employed. Thus, the amount of catalyst can be based on the amount of starter provided to the alkoxylation zone and not the degree of alkoxylation to be effected.

Normally, the modified bimetallic or polymetallic catalyst and the starter component are admixed and then the alkylene oxide is added at the reaction temperature until the desired amount of alkylene oxide has been added, then the product is neutralized if necessary and can be finished, if desired, in any procedure including stripping unreacted starter material from the product mixture, filtration, or further reaction.

The temperature of the alkoxylation is sufficient to provide a suitable rate of reaction and without degradation of the reactants or reaction products. Often, the temperatures range from between about 50° C. and 270° C., e.g. from about 100° C. to 200° C. The pressure may also vary widely, but when low-boiling alkylene oxides such as ethylene oxide and propylene oxide are employed, a pressurized reactor is preferably used.

The alkoxylation reaction medium is preferably agitated to ensure a good dispersal of the reactants and catalyst throughout the reaction medium. Also, the alkylene oxide is usually added at a rate approximating that which it can be reacted.

The present invention provides a preferred procedure whereby a divalent or polyvalent metal or a divalent or polyvalent metal-containing compound as described herein can be effectively used to prepare catalytic species which are active in the alkoxylation of organic compounds having at least one active hydrogen such as alcohols, especially long-chain fatty alcohols, carboxylic acids, amines, polyols and phenols. This is accomplished by the following general procedure.

A first divalent or polyvalent metal-containing composition is prepared by contacting a divalent or polyvalent metal or a divalent or polyvalent metal-containing compound with an activator or an organic compound having at least one active hydrogen under conditions at which the divalent or polyvalent metal or the divalent or polyvalent metal-containing compound and the activator will react or interact to form one or more catalytically active derivatives, i.e., a first divalent or polyvalent metal-containing composition other than a Group IIA or IIIB metal-containing composition, which is then reacted with a second divalent or polyvalent metal-containing composition other than a Group IIA or IIIB metal-containing composition under conditions effective to form one or more catalytically active derivatives, hereinafter referred to collectively as "the catalyst precursor composition". The activator may be any compound having the formula

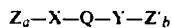

$$Z_a-X-Q-Y-Z'_b$$

wherein the various terms are as previously defined. The modified bimetallic or polymetallic alkoxylation catalysts incorporating the catalyst precursor compositions of this reaction are especially effective in the alkoxylation of alcohols, particularly primary alcohols such as the long-chain fatty alcohols, or mixtures thereof, which are used as starters in the manufacture of nonionic surfactants. However, the modified bimetallic or polymetallic alkoxylation catalysts incorporating the catalyst precursor composition can also be effectively used in the catalytic reaction of a wide variety of organic compounds containing active hydrogen. If, for example, an activator, e.g., ethylene glycol, is used, the catalyst precursor composition can readily be utilized in situ to catalyze the alkoxylation of ethylene glycol itself, thereby producing ethylene glycol-started poly(oxyalkylene)glycols of any desired nominal molecular weight and advantageously having a relatively narrow molecular weight distribution.

If, by way of further example, the organic compound having at least one active hydrogen is 1-dodecanol and the catalyst precursor composition is directly alkoxylated with ethylene oxide, the product will be a mixture of ethoxylates of 1-dodecanol whose composition will be determined by the molar ratio of ethylene oxide to 1-dodecanol.

As used herein, the term "excess activator" means that amount of activator which is not chemically or physically bound to divalent or polyvalent metal(s) other than Group IIA or Group IIIB metals and thus can be removed by simple physical means. The technique employed for this operation is not critical. Vacuum stripping is recommended for its simplicity and efficiency, but evaporation and other known procedures may also be used.

The catalyst precursor composition will be obtained as a finely divided, particulate solid, in slurry form, which can be readily separated from the reaction mixture by filtration, decantation, or similar procedures. The product so obtained is catalytically active in alkoxylation reactions, whether or not modified with a divalent or polyvalent oxyacid or a divalent or polyvalent metal salt of an oxyacid.

It is a particularly desirable feature of this invention that the catalyst can be used to provide alkoxylate surfactants having a uniquely narrow molecular weight distribution, low pour point, and low level of unreacted starter component. In this usage, the catalyst is contacted with the starter component, e.g., alcohol, under conditions at which reaction will occur, to perform an alcohol-exchange (which can also be referred to as an alkoxide exchange) reaction. A portion of the starter alcohol thus is present as an alcoholate of a divalent or polyvalent metal, which alcoholate is itself an active species for the alkoxylation reaction. This reaction mixture is then reacted with one or more alkylene oxides, e.g., alkylene oxides such as ethylene oxide, according to known procedures to produce the desired surfactant.

Referring now to the structural formula given above for the activator, X and Y are preferably more than one carbon removed from each other, e.g., in the beta position relative to each other, and are preferably oxygen, as in ethylene glycol, or oxygen and nitrogen, as in monoethanolamine; however, X and Y can also be sulfur or phosphorous. Exemplary of other useful compounds are ethylenediamine, N-methylethanolamine, tetrahydrofurfuryl alcohol, 2-mercaptoethanol, 1,2-propylene glycol, 2-methylthioethanol, 2-ethoxyethanol, diethylene glycol, 1,3-propanediol and 1,4-butanediol.

Z and Z' are the same or different radicals, optionally substituted, and often at least one of Z and Z' is selected from the group consisting of hydrogen, lower linear or branched alkyl of one to four carbon atoms, alkylene from two or about six carbon atoms, phenyl or lower alkyl-substituted phenyl, cycloalkyl of three to about six carbon atoms and alkylene or heteroatom-substituted alkylene rings.

In the activator, Q may comprise a carbon chain of up to six carbons between X and Y. A two-to four-carbon chain is preferred, however, because the activating capacity of X and Y is maximized at such chain lengths. Of these, a two-carbon chain length is especially preferred. In highly preferred embodiments, Q will be a two-carbon chain and the structural formula will be as follows:

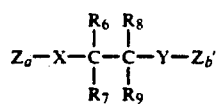

$$Z_a-X-\underset{\underset{R_7}{|}}{\overset{\overset{R_6}{|}}{C}}-\underset{\underset{R_9}{|}}{\overset{\overset{R_8}{|}}{C}}-Y-Z'_b$$

wherein Z, Z', X, Y, a and b are as defined hereinabove and $R_6$, $R_7$, $R_8$, and $R_9$ are preferably hydrogen, but may also be lower alkyl or alkylene groups of one to four carbon atoms, optionally substituted, or such other radicals as do not interfere with the usefulness of the activator for its intended purpose.

Also, Q may be cyclic, preferably cycloalkyl of six or fewer carbons, optionally substituted, as can be represented by the formula:

Compounds coming within this description would include 4-methoxycyclohexane 1,2-diol; 2-aminocyclopentanol; and 2-methoxycyclopentanol.

Similarly, either X or Y or both of them could be part of a ring structure with a carbon atom adjacent to either of them, as illustrated by the formula:

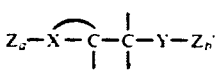

Some compounds illustrating such configurations would include tetrahydrofurfuryl alcohol; furfuryl alcohol; 2-hydroxyethyl aziridine; 1-(N-methyl-2-pyrrolidinyl) ethanol; and 2-aminomethylpyrrolidine Moreover, X and Y can themselves be part of the same ring structure, including Q, according to the formula:

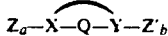

Exemplary of such compounds would be piperazine; 4-hydroxymethyl-2,2-dimethyl-1,3 dioxolane; 2,6-dimethylmorpholine; and cyclohexanone ethylene ketal.

Numerous other ring structures, whether saturated or unsaturated, substituted or unsubstituted, are also possible and are intended to be within the scope of the present invention.

The only perceived limitation on Q and on the overall structure of the formula is that the activator must be capable of solubilizing, at least in part, the divalent or polyvalent metal-containing compound. In some instances, solubilization is considered to be an important step which permits certain inoperable materials to be successfully utilized. Without intending to be bound to any particular theory, this solubilization is believed to be accomplished through the electron-withdrawing effects of heteroatoms X and Y in relation to adjacent carbon atoms. This allows the formation of complexes with the divalent or polyvalent metal, such as exemplified by the structure:

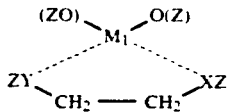

It is understood that the valency requirements of $M_1$ in the above structure are appropriately satisfied by (ZO) and O(Z).

Thus, any structure represented by the formula

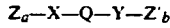

is satisfactory, provided only that it does not eliminate or neutralize the electronegativity of the heteroatoms and thus prevent the activator from performing its intended purpose of solubilizing, at least in part, the divalent or polyvalent metal-containing compound. In the method for preparing the modified bimetallic or polymetallic catalysts of this invention, it is believed that the activator may provide a stabilizing effect, e.g., thermal stability at high temperatures, for certain intermediate catalytic species prepared in said method, thereby permitting formation of the desired final catalytically active species.

In the solubilizing step of the process of this invention, as has been mentioned above, a divalent or polyvalent metal-containing compound or mixtures thereof are mixed with the activator or the organic compound having at least one active hydrogen to form one or more divalent or polyvalent metal-containing composition species. The purpose of this treatment is to solubilize sufficient divalent or polyvalent metal-containing compound to be catalytically effective in an alkoxylation reaction; thus, the metal-containing compound concentration could be either below or above its solubility maximum in the activator, provided only that sufficient metal-containing compound is solubilized to be catalytically effective. As a general guideline, however, the concentration of divalent or polyvalent metal-containing compound used in the initial step should typically be in the range of about 1-2%, based on the organic compound employed. Concentrations exceeding about 30% would rarely be considered desirable.

The temperature for this procedure is not considered critical, and can range from about 50° C. up to the boiling point of the organic compound used, typically well over 200° C. It is desirable to operate in the range of about 90° to 150° C., preferably about 125° to 150° C., and the system can be put under either vacuum or pressure to maintain any desired temperature while maintaining the activator in the liquid phase. Advantageously, the conditions of temperature and pressure are such that byproducts of reaction can be vaporized and removed from the reaction medium. Preferably the catalyst preparation is conducted under a substantially inert atmosphere such as a nitrogen atmosphere.

To perform this step of the process, a first divalent or polyvalent metal-containing compound as described herein is simply added to the activator or the organic compound having at least one active hydrogen in a stirred vessel under sufficient agitation to create a slurry of the metal-containing compound for a period of time adequate to solubilize at least a portion of the metal-containing compound. Normally, this will be accomplished within a period of about 1 to 4 hours. The amount of metal-containing compound which will be solubilized will depend, of course, on the concentration of metal-containing compound present, the effectiveness of the activator used, and on the temperature, time and agitation employed. Ideally, the quantity of first divalent or polyvalent metal-containing compound desired for the subsequent alkoxylation reaction is solubilized. The source of the first divalent or polyvalent metal-containing compound for this step can include any commercially-available grade of metal-containing compound, since minor impurities contained in such metal-containing compounds are not believed to significantly adversely affect the catalyst formed by the procedures of this invention.

To prepare the second divalent or polyvalent metal-containing composition, an appropriate second divalent or polyvalent metal-containing compound, e.g., a metal acetate, described hereinbelow can be reacted with an organic compound having at least one active hydrogen. The resulting mixture will be heated at reflux at a temperature of from about 80° C. to about 200° C. by adjusting pressure on the reaction system. Normally, such heating will be accomplished within a period of about 2 to 6 hours while concurrently removing byproducts of reaction, e.g., water, isopropanol, etc., overhead.

It is understood that bimetallic and polymetallic salts can be used in the processes of this invention. For example, the first and second divalent or polyvalent metal-containing compounds other than Group IIA or IIIB metal-containing compounds can be the same compound for purposes of this invention. Illustrative of such bimetallic or polymetallic salts include, for example, zinc tungstate ($ZnWO_4$), aluminum titanate ($Al_2TiO_5$) and the like.

The first divalent or polyvalent metal-containing composition is then reacted with the second divalent or polyvalent metal-containing composition under effective conditions to produce a catalyst precursor composition which is reacted with a divalent or polyvalent acid or a divalent or polyvalent metal salt of an oxyacid to produce a catalyst for alkoxylation reactions and enhance the narrowness of the alkoxylation product. This would be the case where, for example, ethylene oxide is to be added to the material used as the activator, e.g., ethylene glycol, to produce poly(oxyethylene)-glycols of any desired molecular weight.

The first and second divalent or polyvalent metal-containing compositions used in this invention can be represented by the formulae $[R_1X_1]_m$ $[M_1]_n$ and $[R_2X_2]_{m'}$ $[M_2]_{n'}$, wherein $R_1$, $R_2$, $X_1$, $X_2$, $M_1$ and $M_2$ are as defined hereinabove and m, n, m' and n' are the same or different integers satisfying the appropriate valency requirements. The divalent or polyvalent metal-containing compositions can be prepared by contacting a divalent or polyvalent metal other than a Group IIA or IIIB metal described hereinabove or other suitable source of divalent or polyvalent metal with an organic compound containing an active hydrogen atom of the formulae $R_1X_1H$ or $HX_2R_2$. Such divalent or polyvalent metal-containing compositions can be prepared by conventional methods.

Illustrative of the second divalent or polyvalent metal-containing compounds/compositions for use in this invention include soluble divalent or polyvalent metal-containing compounds/compositions per se or divalent or polyvalent metal-containing compounds/compositions which can be converted to a soluble form upon interaction with the alkoxylation process reactants, e.g., activator. Examples of specific second divalent or polyvalent metal-containing compounds/compositions include one or more reaction products of the divalent or polyvalent metal other than a Group IIA or IIIB metal with various alcohols (alcoholates such as aluminum alkoxides and phenoxides) as well as oxide, hydroxide, ammoniate, amide, thiolate, carbide, thiophenoxide, nitride, thiocyanate and carboxylate compounds, e.g., acetates, formates, oxalates, citrates, benzoates, laurates and stearates.

The reaction of the first divalent or polyvalent metal-containing composition with the second divalent or polyvalent metal-containing composition is conducted under effective conditions to produce a catalyst precursor composition. This reaction can be conducted by conventional methods such as described in U.S. Pat. Nos. 3,432,445, 3,607,785 and 4,281,087. Alternatively, the catalyst precursor composition can be prepared from a Meerwein double alkoxide by controlled hydrolysis/solvolysis. See Bradley, D. C., Mehrotra, R. C. and Gaur, D. D., Metal Alkoxides, Academic Press, Inc., New York, N.Y. (1978) and also Teyssie, Ph., Bioul, J. P., Hocks, L. and Ouhadi, T., Chemtech (1977), pp. 192-194.

If the catalyst is to be used to produce a surfactant or other alkoxylation product using a different starter, an exchange can be performed as described above. For example, in producing a surfactant, the catalyst of formula (i) hereinabove can be added to a stirred vessel containing a surfactant range alcohol or mixture of such alcohols, typically $C_{12}$-$C_{14}$ alcohols. The concentration of catalyst precursor composition or the modified bimetallic or polymetallic catalyst composition used can vary over a very broad range, but ideally would be approximately that desired for the subsequent alkoxylation reaction. The temperature during the exchange reaction may be any temperature at which the reaction will occur, but, preferably, will be in the range of about 80°-250° C., and pressure may be adjusted to achieve these temperatures. If the exchange procedure is followed, the organic compound chosen should have a boiling point of less than about 200° C. to permit it to be readily stripped from the detergent alcohol, most of which boil in the 250° C. range or higher. The resulting alcohol-exchanged product is suitable for use directly as a catalyst in alkoxylation reactions to produce surfactants started with the exchanged alcohol or alcohols.

The catalyst produced by the above-described process is often in the form of a stable slurry of finely divided (e.g., about 5 microns) particles, and containing excess divalent or polyvalent metal-containing compound.

The catalyst precursor composition of formula (ii) hereinabove, including the alcohol-exchanged product thereof, is modified with a divalent or polyvalent oxyacid or a divalent or polyvalent metal salt of an oxyacid prior to use as catalyst for alkoxylation to provide a narrow distribution of alkoxylate products. Mixtures of divalent or polyvalent oxyacids and/or mixtures of divalent or polyvalent metal salts of oxyacids, or cross combination mixtures thereof, can be used in the processes of this invention. The modifier can be added at any time during the catalyst preparation but generally is added prior to the addition of a detergent-range alcohol and may be added as a solid or dissolved in an appropriate solvent. While the precise chemical nature of this procedure is not fully understood, the modification does result in a demonstrable improvement to the overall process in that the molecular weight distribution is narrowed and/or the catalytic activity is enhanced. In addition, modified catalysts tend to require little or no induction period in the alkoxylation reaction, and also may increase the reaction rate over that of their unmodified counterparts. In contrast, addition of a divalent or polyvalent oxyacid or a divalent or polyvalent metal salt of an oxyacid to conventional catalysts, such as potassium hydroxide, slows the alkoxylation rate while producing no beneficial effect on the product distribution.

Alternatively, the modified bimetallic or polymetallic catalysts may be prepared by contacting a divalent or polyvalent metal-containing compound as described herein with an activator or an organic compound having at least one active hydrogen under conditions at which the divalent or polyvalent metal-containing compound and the activator or organic compound will react or interact to form one or more catalytically active derivatives, which are then reacted with a divalent or polyvalent metal salt of an oxyacid other than a Group IIA or IIIB metal salt of an oxyacid under conditions effective to form one or more modified alkoxylation catalysts. See copending U.S. patent application Ser. No. (D-15752), filed on an even date herewith, and incorporated herein by reference.

Advantageous results can be obtained if the catalyst is used in its "crude" form, i.e., without separation from its reaction mixture or purification. Nevertheless, if desired, the catalyst, whether modified or not, can be separated from its reaction mixture, purified, dried and stored. Such may be accomplished in a straightforward manner, as by stripping off the excess activator or other organic material containing active hydrogen, filtering the resulting slurry, reslurrying the wet solids with a solvent (e.g., tetrahydrofuran) and refiltering, and drying, preferably under vacuum. The solids thus obtained will be catalytically active, but, frequently, they are substantially less active than the catalyst in its "crude" form. Reaction rate notwithstanding, however, the desired narrow molecular weight distribution and other benefits can still be obtained.

It is a highly desirable, and quite unexpected, benefit of this aspect of the invention that the overall process embodied in the various procedures described above for making catalysts from certain divalent or polyvalent metals other than Group IIA or IIIB metals is remarkably "forgiving" of process variations. Thus, considerable flexibility exists as to the point modifier is added and, within reasonable limits, how much modifier is used. Similarly, the unreacted organic compound may be removed wholly or partially prior to, e.g., an exchange reaction, if used, or it may be left present during the exchange reaction. Moreover, the catalyst may be re-used indefinitely, used and stored in its "crude" form, or purified and dried, with any loss in reaction rate made up by increasing temperature.

The procedures involved in carrying out the process of this invention are illustrated by the following description directed toward the manufacture of nonionic surfactants.

The manner in which the process of this invention is practiced can be illustrated by the following generalized procedure for preparing a slurry of modified bimetallic or polymetallic alkoxylation catalyst intended for use in the manufacture of "peaked" (narrow molecular weight distribution) linear alcohol ethoxylates (nonionic surfactants).

As applied to the specific case of the production of nonionic surfactants, the process of this invention is characterized by a considerable degree of operational latitude. This is particularly true in the preferred version of the process wherein the modified form of the catalyst is produced. From the standpoint of the chemistry which takes place, there are five distinct steps in the preferred preparation of the modified bimetallic and polymetallic catalysts. Steps, 1, 2, 3 and 4 involve the following reactions:

| | |
|---|---|
| Step 1 | Reaction of a divalent or polyvalent metal other than a Group IIA or IIIB metal or a metal-containing compound other than a Group IIA or IIIB metal-containing compound with a suitable activator or an organic compound having at least one active hydrogen to produce a first divalent-polyvalent metal-containing composition. |
| Step 2 | Reaction of a divalent or polyvalent metal other than a Group IIA or IIIB metal or other suitable source of divalent or polyvalent metal other than a Group IIA or IIIB metal source with an organic compound containing at least one active hydrogen to produce a second divalent or polyvalent metal-containing |
| Step 3 | Reaction of the first divalent or polyvalent metal-containing composition with the second divalent or polyvalent metal-containing composition to produce a catalyst precursor composition. |

| | |
|---|---|
| Step 4 | Reaction of the catalyst precursor composition with a detergent range alcohol to effect exchange of the activator-derived organic radicals for detergent-range alcohol-derived organic radicals. |

During or following the exchange reactions of step 4 the organic compound, which preferably is substantially more volatile than the detergent-range alcohol, is removed from the system by distillation. At the conclusion of this operation, the unmodified version of the catalyst is obtained in the form of an residue-free slurry in the detergent-range alcohol.

In the preparation of the intermediate unmodified form of the bimetallic or polymetallic catalyst, steps 1 and 2 may be combined into one operation. The first and second divalent or polyvalent metal-containing compositions prepared in steps 1 and 2 may be the same compositions, thereby omitting step 2. Additionally, steps 1 and 4, above, may be combined into one operation wherein the divalent or polyvalent metal or the divalent or polyvalent metal-containing compound is reacted with a mixture of activator or organic compound and detergent-range alcohol. Alternatively, step 2 may be omitted and a divalent or polyvalent metal salt of an oxyacid used in step 5 below which is other than a Group IIA or IIIB metal salt of an oxyacid. The procedure of combining steps 1 and 4 may be employed because it tends to minimize color build-up in the catalyst slurry. From the standpoint of the final product characteristics, both procedures are equally acceptable. Modified processes wherein the activator is fed into a slurry of the detergent-range alcohol and the divalent or polyvalent metal base or the detergent-range alcohol is fed into a slurry (or, in some cases, a solution) of the divalent or polyvalent metal base in the activator are also operationally viable, although their use offers no perceived advantage over the batch-charging version.

The preparation of the modified catalyst involves a fifth major processing operation which, like that of steps 1 through 4, is a distinct step in terms of the chemistry which takes place.

| | |
|---|---|
| Step 5 | Treatment of the slurry of unmodified catalyst in detergent-range alcohol with a deficiency of some appropriate modifier such as a divalent or polyvalent oxyacid or a divalent or polyvalent metal salt of an oxyacid or mixtures thereof. |

This step provides a highly-active, modified bimetallic or polymetallic catalyst in the form of a slurry in the detergent-range alcohol. The product slurry is normally subjected to an in vacuo drying operation before it is employed in an ethoxylation reaction to manufacture a nonionic surfactant. The modifier charge can be based either upon the initial divalent or polyvalent metal-containing compound charge or, upon an "active catalyst" value which is obtained by titrating a sample of the divalent or polyvalent metal-containing compound/activator reaction mixture for alkalinity content using 0.01N alcoholic HCl in the presence of bromothymol blue indicator. When a divalent or polyvalent oxyacid is employed, it is convenient to use the above procedure. A convenient procedure may be to follow the course of the divalent or polyvalent metal-containing compound- /activator reaction by titration and to base the modifier charge upon the alkalinity value obtained when a constant level of alkalinity has been reached. Such a convenient procedure, for example, may be to add the modifier at a level of about 50% of this "constant" alkalinity value. Monitoring of this reaction by titration and ultimately determining the modifier charge based upon this analysis, although a used procedure, it cannot be used with amino-functional activators because the amine functionality interferes with the alkalinity analysis. In such instances, the preferred procedure is to base the modifier charge on the alkalinity value obtained by titrating the residue-free (stripped) slurry of catalyst in detergent alcohol.

Because of the fact that this process offers such wide operational latitude, there is no single procedure which can be said to represent the general procedure. This consideration notwithstanding, one procedure which will suffice to illustrate the process is as follows:

A divalent or polyvalent metal-containing compound other than a Group IIA or IIIB metal-containing compound (as commercially supplied) and 2-ethoxyethanol (available from Union Carbide Corporation, Danbury, Conn.) are charged to a suitably-sized, agitated vessel equipped with a reflux condenser, thermocouple, 10-tray distillation column, and inert gas purge inlet. The reactants are charged in weight ratios ranging from 60 to 80 parts of 2-ethoxyethanol to one part of the divalent or polyvalent metal-containing compound. The charge is heated under a nitrogen purge for a period of 2 to 6 hours at the reflux temperature (about 135° C.) while refluxing solvent is removed overhead continuously or intermittently at a make rate sufficiently slow such that during the entire reaction period only about 10 to 15% of the original solvent charge is removed overhead. The purpose of this operation is to remove from the system water which was either introduced with the reactants or produced by chemical reaction. The usual time period for this procedure is about 4 hours.

The resulting first divalent or polyvalent metal-containing composition is then reacted with a second divalent or polyvalent metal-containing composition other than a Group IIA or IIIB metal-containing composition to produce a catalyst precursor composition. For example, a mixture of aluminum isopropoxide in isopropanol is added to the first divalent or polyvalent metal-containing composition and heated at reflux (ca. 80° C.) for a period of about 2 to 6 hours under nitrogen while concurrently removing isopropanol overhead. After a constant head temperature is maintained, corresponding to 2-ethoxyethanol (ca. 135° C.), the heat is removed and the reaction mixture allowed to cool to ambient temperature.

At this point the reaction mixture is diluted with the detergent range alcohol to be ethoxylated; typically the quantity of alcohol added is about 100 grams/gram of metal-containing compound (calculated as metal-containing compound) used in the initial reaction. The resulting mixture is cooled to about 75° C. and treated, under agitation, with sufficient modifier, such as phosphoric acid or a metal phosphate, to modify about 50% (on an equivalents basis) of the catalyst precursor reaction mixture.

The temperature is then increased to permit removal of the undesired organic compounds from the reaction mixture by distillation. Distillation is continued until the kettle temperature reaches about 215° to 225° C. and both the kettle product and the distillate are free of residue as indicated by gas chromatographic (GC) analysis (e.g., less than 1000 ppm by weight and often less than 100 ppm by weight).

The thus-obtained slurry of catalyst in detergent alcohol can either be used directly as a charge to the ethoxylation reactor or, optionally, diluted with sufficient, dry detergent-range alcohol to afford any desired catalyst concentration in the slurry.

The above procedure represents but one of many equally viable versions of this process. Other versions are possible through combinations of the options available in the various process steps.

The catalytic alkoxylation reactions of this invention can be effected, for example, by conventional methods such as (1) batch processes; (2) continuous fixed-bed processes; and (3) continuous fluidized reactor processes. In a batch reactor, the catalyst is kept suspended in the reactant by shaking or stirring. In a fluidized reactor, the catalyst is at a particular original level. As the velocity of the reactant stream is increased, the catalyst bed expands upward to a second level, and at a critical velocity it enters into violent turbulence. The fluidized reactor is particularly useful for removing or supplying the heat necessary to maintain a fixed catalyst temperature. The fluidized reactor can usually be employed only on a rather large scale since good fluidization requires a reactor larger than about 1.5 inches in diameter.

The processes of this invention broadly involve the use of modified bimetallic or polymetallic catalysts for the alkoxylation of active-hydrogen compounds, preferably hydroxyl-containing compounds, such as, primary or secondary alcohols, diols or triols. Mixtures of active-hydrogen compounds can be used.

Alkoxylation product mixtures prepared by the processes of this invention comprise alkoxylation species that can be represented by the formula

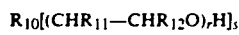

$$R_{10}[(CHR_{11}-CHR_{12}O)_rH]_s$$

wherein $R_{10}$ is an organic residue of an organic compound having at least one active hydrogen, s is an integer of at least 1 up to the number of active hydrogens contained by the organic compound, $R_{11}$ and $R_{12}$ may be the same or different and can be hydrogen and alkyl (including hydroxy- and halo-substituted alkyl) of, for example, 1 to 28 carbons, and r is an integer of at least 1, say, 1 to about 50.

Organic compounds having active hydrogens include alcohols (mono-, di- and polyhydric alcohols), phenols, carboxylic acids (mono-, di- and polyacids), and amines (primary and secondary). Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms. The organic compounds having active hydrogens can be the product of hydroformylation/hydrogenation reactions.

Particularly preferred alcohols are primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenyls of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

The alkylene oxides which provide the oxyalkylene units in the ethoxylated products include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorhydrin and epibromhydrin. The preferred alkylene oxides are ethylene oxide and propylene oxide.

The selection of the organic residue and the oxyalkylene moieties is based on the particular application of the resulting alkoxylation product. Advantageously, narrow distributions can be obtained using a wide variety of compounds having active hydrogens, especially monohydric alcohols, which provide desirable surfactants. Because of the narrow distribution of the alkoxylation product mixture, especially attractive alkoxylation products are surfactants in which certain hydrophilic and lipophilic balances are sought. Hence, the organic compound often comprises a monohydric alcohol of about 8 to 20 carbons and the alkylene oxide comprises ethylene oxide.

While the processes described herein are capable of selectively providing narrow distributions of alkoxylates with the most prevalent having as low as one mole of oxyalkylene per mole of active hydrogen site, a particular advantage exists in the ability to provide a narrow distribution at higher levels of alkoxylation, e.g., wherein the most prevalent specie has at least 4 oxyalkylene units. For some surfactant applications, the most prevalent alkoxylation specie has 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation is narrow, but not so narrow that a range of activity is lost.

Moreover, the relatively symmetrical distribution of alkoxylate species that can be provided by this invention enhances that balance while providing a mixture that exhibits desirable physical properties such as cloud point, freeze point, viscosity, pour point and the like. For many alkoxylation mixtures of this invention, the species falling within the range of $\bar{n}$ plus or minus two comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 18 to about 30 weight percent, e.g., about 22 to 28, weight percent, to enhance the balance of the composition.

Another class of alkoxylation product mixtures are the poly(oxyethylene)glycols. For instance, triethylene glycol and tetraethylene glycol find application in gas dehydration, solvent extraction and in the manufacture of other chemicals and compositions. These glycols can be prepared by the ethoxylation of ethylene glycol and diethylene glycol. Advantageous processes of this invention enable ethoxylate product compositions containing at least about 80, say, about 80 to 95, weight percent of triethylene glycol and tetraethylene glycol.

Among the most commercially important alkoxylation products are those which utilize water or an alcohol (monols, glycols, polyols, etc.) as starter (initiator) and ethylene oxide, propylene oxide, or an ethylene oxide/propylene oxide mixture as the 1,2-alkylene oxide monomer. Such alcohol ethoxylates encompass a myriad of structures, compositions and molecular weights intended for service in a diversity of applications ranging from heavy duty industrial end uses such as solvents and functional fluids to ultra-sophisticated, consumer-oriented end uses such as in pharmaceutical, personal care and household goods. The modified bimetallic or polymetallic catalysts of the instant invention find utility in the manufacture of a broad range of alkoxylation products, but are particularly useful in the manufacture of alkoxylates designed for service in sophisticated, consumer-oriented end use areas of application where product quality demands are stringent. Among the many types of alkoxylates which are used in such applications, two of the most prominent are the poly(oxyethylene)glycols and the fatty alcohol ethoxylates. The poly(oxyethylene)glycols, known under such tradenames as CARBOWAX ®, POLYGLYCOL E ®, PLURACOL E ®, etc., are manufactured by ethoxylation of ethylene glycol or one of its homologues; they are produced over a molecular weight range of about 200 to about 8,000. The fatty alcohol ethoxylates, known under such non-ionic surfactant tradenames as NEODOL ®, ALFONIC ®, TERGITOL ®, etc., are manufactured by ethoxylation of linear or branched $C_{10}$-$C_{16}$ saturated alcohols; they are produced over a molecular weight range of about 300 to about 800. It is in the production of these and other performance type, premium quality ethoxylates that the modified bimetallic or polymetallic catalysts of the instant invention offer maximum advantages relative to the usual homogeneous ethoxylation catalysts (NaOH, KOH, etc.).

This invention can be illustrated by the following examples.

EXAMPLE 1

Into a 1-liter reaction flask equipped with a reflux condenser, thermocouple, mechanical stirrer and a gas purge inlet was added 300 grams of Alfol ® 1214, a mixture of $C_{12-14}$ linear, fatty acohols (approximately 55/45 weight ratio) commercially available from Vista Chemical Company, Houston, Tex., and 20.7 grams of zinc octoate. The mixture temperature was adjusted to 28° C. and 2.2 grams (0.019 moles) of 86 percent phosphoric acid were added to the flask. The mixture was then stirred for a period of 85 minutes. The reaction mixture was then heated under vacuum (1 millimeter) and 46 grams of Alfol® 1214 was removed overhead. When the kettle temperature reached 135° C., the heat was removed and the contents allowed to cool to ambient temperature under a nitrogen blanket until use. A quantity of this catalyst was used to make a batch preparation of a nonionic surfactant as described in Example 3 hereinafter.

EXAMPLE 2

Into a 1-liter reaction flask equipped with a reflux condenser, thermocouple, mechanical stirrer and a gas purge inlet was added 515 grams of Alfol® 1214, a mixture of $C_{12-14}$ linear, fatty alcohols (approximately 55/45 weight ratio) commercially available from Vista Chemical Company, Houston, Tex., and 20.7 grams of zinc octoate. The resulting mixture was heated at a temperature of 35° C. for a period of 20 minutes, then 12.1 grams of aluminum isopropoxide was added. This mixture was stirred for a period of 3 hours at a temperature of 80°-95° C. At a temperature of 90° C., 2.2 grams (0.019 moles) of 86 percent phosphoric acid were added to the flask. The mixture was stirred for a period of 90 minutes at a temperature of 90° C. and thereafter was allowed to stand for a period of 2 days under nitrogen. The reaction mixture was then heated under vacuum (3–4 millimeters) and approximately 100 grams of Alfol® 1214 was removed overhead. When the kettle temperature reached 142° C., the heat was removed and the contents allowed to cool to ambient temperature under a nitrogen blanket until use. A quantity of this catalyst was used to make a batch preparation of a nonionic surfactant as described in Example 4 hereinafter.

EXAMPLES 3 AND 4

The general procedure described hereinabove was used to produce nonionic surfactants. The reactors for these preparations were a 400 cubic centimeter stirred autoclave equipped with an automatic ethylene oxide feed system (Example 3) and a 2 gallon stirred autoclave equipped with an automatic ethylene oxide feed system (Example 4) wherein a motor valve controlled the feed of ethylene oxide to maintain about 60 psig pressure. Into the 2 gallon stirred autoclave was added Alfol® 1214, ethylene oxide and a catalyst slurry specified in Table A below in the amounts specified in Table A. These reactions were conducted under a nitrogen atmosphere (20 psig) at a temperature of 160° C. The ethylene oxide feed time and maximum reaction rate are also specified in Table A. The molecular weight distribution of the nonionic surfactant products was determined by gas chromatographic analysis (weight %) and the results are given in Table A.

TABLE A

| Preparation of Nonionic Surfactants | | |
|---|---|---|
| | Example | |
| | 3 | 4 |
| Ethoxylation Process | | |
| Alfol ® 1214 (grams) | 101 | 80 |
| Ethylene oxide (grams) | 205 | 736 |
| Catalyst prepared in Example No. | 1 | 2 |
| Catalyst (grams) | 30 | 420 |
| Ethylene oxide feed time (minutes) | 540 | 345 |
| Maximum reaction rate (grams/minute) | 1.2 | 3.0 |
| Product Molecular Weight Distribution | | |
| $E_0$ | 0.3 | 0.6 |
| $E_1$ | 0.5 | 0.8 |
| $E_2$ | 1.4 | 2.3 |
| $E_3$ | 3.7 | 5.5 |
| $E_4$ | 8.0 | 10.6 |
| $E_5$ | 13.8 | 16.0 |
| $E_6$ | 18.2 | 18.9 |
| $E_7$ | 19.2 | 18.6 |
| $E_8$ | 15.4 | 13.8 |
| $E_9$ | 10.6 | 8.4 |
| $E_{10}$ | 5.9 | 3.5 |
| $E_{11}$ | 2.5 | 0.8 |
| $E_{12}$ | 0.6 | 0.1 |

The results from Table A demonstrate the effectiveness of zinc-containing and aluminum-containing bimetallic or polymetallic catalysts modified with phosphoric acid. As illustrated by Examples 3 and 4, nonionic surfactants were prepared having a narrow distribution of alkoxylation species with at least one alkoxylation specie constituting at least about 18 weight percent of the product mixture.

Although the invention may have been illustrated by the preceding examples, it is not to be construed as being limited thereby; but rather, the invention encompasses the generic area as hereinbefore disclosed. Various modifications and embodiments can be made without departing from the spirit and scope thereof.

What is claimed is:
1. A method for providing an alkoxylation catalyst comprising:
 (a) reacting or solubilizing, at least partially, a first divalent or polyvalent metal or metal-containing compound wherein said metal is selected from the group consisting of either (i) boron, aluminum, gallium, indium, thallium, titanium, zirconium, hafnium, vanadium, niobium, tantalum, chromium, molybdenum, tungsten, manganese, iron, cobalt, nickel, copper, and zinc, or (ii) carbon, silicon, germanium, tin, lead, titanium, zirconium, hafnium, vanadium, niobium, tantalum, chromium, molybdenum, tungsten, manganese, iron, cobalt, nickel, copper and zinc, by mixing with an activator having the formula:

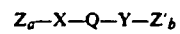

$$Z_a-X-Q-Y-Z'_b$$

wherein X and Y are the same or different electronegative, heteroatoms selected from the group consisting of oxygen, nitrogen, sulfur and phosphorus; a and b are the same or different integers satisfying the valency requirements of X and Y; Q is an organic radical which is electropositive or essentially neutral relative as to X and/or Y; Z and Z' are the same or different and are either hydrogen or an organic radical which does not prevent said reacting or solubilizing, thereby forming a first divalent or polyvalent metal-containing composition;
(b) reacting a second divalent or polyvalent metal or a second divalent or polyvalent metal-containing compound wherein said metal is selected from the group consisting of either (i) boron, aluminum, gallium, indium, thallium, titanium, zirconium, hafnium, vanadium, niobium, tantalum, chromium, molybdenum, tungsten, manganese, iron, cobalt, nickel, copper, and zinc, or (ii) carbon, silicon, germanium, tin, lead, titanium, zirconium, hafnium, vanadium, niobium, tantalum, chromium, molybdenum, tungsten, manganese, iron, cobalt, nickel, copper and zinc, with an organic compound having at least one active hydrogen to produce a second divalent or polyvalent metal-containing composition;
(c) reacting the first divalent or polyvalent metal-containing composition with the second divalent or polyvalent metal-containing composition under effective reaction conditions to produce a catalyst precursor composition; and
(d) reacting the catalyst precursor composition with a divalent or polyvalent oxyacid or a divalent or polyvalent metal salt of an oxyacid or mixtures thereof under effective reaction conditions to produce the alkoxylation catalyst; provided that when the first divalent or polyvalent metal or metal-containing compound is selected from (i), the second divalent or polyvalent metal or metal-containing compound is selected from (ii), and further provided that when the first divalent or polyvalent metal or metal-containing compound is selected from (ii), the second divalent or polyvalent metal or metal-containing compound is selected from (i).

2. The method of claim 1 wherein steps (a) and (b) are combined into one step.

3. The method of claim 1 wherein the first divalent or polyvalent metal-containing compound is selected from oxides, hydroxides, carboxylates, alcoholates, ammoniates, amides, nitrides, thiocyanates, thiolates, carbides, thiophenoxides and substances to which said compounds are converted in situ in said method.

4. The method of claim 3 wherein the first divalent or polyvalent metal-containing compound is a carboxylate selected from acetates, formates, oxalates, citrates, benzoates, laurates, stearates and substances to which said compounds are converted in situ in said method.

5. The method of claim 1 wherein the first divalent or polyvalent metal-containing compound is an aluminum-containing compound.

6. The method of claim 1 wherein the first divalent or polyvalent metal-containing composition is an aluminum-containing alcoholate or an aluminum-containing carboxylate.

7. The method of claim 1 wherein the activator has the formula:

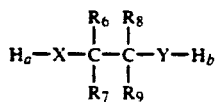

wherein $R_6$, $R_7$, $R_8$ and $R_9$ are the same or different and are selected from the group consisting of hydrogen and lower alkyl or alkylene groups of one to four carbon atoms.

8. The method of claim 1 wherein the activator is ethylene glycol.

9. The method of claim 1 wherein the activator is 2-ethoxyethanol.

10. The method of claim 1 wherein the divalent or polyvalent metal salt of an oxyacid is a metal phosphate.

11. The method of claim 1 wherein the divalent or polyvalent metal salt of an oxyacid is a mixture of a metal sulfate and a metal phosphate.

12. The method of claim 1 wherein the divalent or polyvalent oxyacid is phosphoric acid.

13. The method of claim 1 wherein the divalent or polyvalent oxyacid is a mixture of sulfuric acid and phosphoric acid.

14. The method of claim 1 wherein the second divalent or polyvalent metal-containing compound is selected from oxides, hydroxides, carboxylates, alcoholates, ammoniates, amides, nitrides, thiocyanates, thiolates, carbides, thiophenoxides and substances to which said compounds are converted in situ in said method.

15. The method of claim 14 wherein the second divalent or polyvalent metal-containing compound is a carboxylate selected from acetates, formates, oxalates, citrates, benzoates, laurates, stearates and substances to which said compounds are converted in situ in said method.

16. The method of claim 1 wherein the second divalent metal-containing composition is a metal-containing alcoholate.

17. The method of claim 1 wherein the second divalent or polyvalent metal-containing composition contains a metal selected from aluminum, zinc, zirconium and titanium.

18. The method of claim 1 comprising the additional step of reacting the alkoxylation catalyst with an alcohol under conditions at which an alcohol exchange reaction occurs with the alkoxylation catalyst, thereby producing a corresponding alcohol derivative.

19. The method of claim 18 wherein the alcohol is n-dodecanol.

20. The method of claim 18 wherein the alcohol is a mixture of $C_{12}$–$C_{14}$ alcohols.

21. The method of claim 18 wherein the alcohol is a product of a hydroformylation/hydrogenation reaction.

22. The method of claim 1 comprising the additional step of removing some or all activator which is not bound to the divalent or polyvalent metals.

23. The method of claim 1 wherein about 25 to about 90% of the normal equivalence of the divalent or polyvalent oxyacid or the divalent or polyvalent metal salt of an oxyacid to the first and second divalent or polyvalent metals is added during step (d).

24. An alkoxylation catalyst prepared by the method of claim 1.

25. An alkoxylation catalyst prepared by the method of claim 18.

26. An alkoxylation catalyst having the formula:

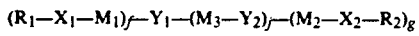

wherein:
$R_1$ and $R_2$ are independently hydrogen or an organic residue of an organic compound having at least one active hydrogen;
$X_1$ and $X_2$ are independently oxygen, sulfur or nitrogen;

$M_1$, $M_2$ and $M_3$ are independently a divalent or polyvalent metal selected from the group consisting of either (i) boron, aluminum, gallium, indium, thallium, titanium, zirconium, hafnium, vanadium, niobium, tantalum, chromium, molybdenum, tungsten, manganese, iron, cobalt, nickel, copper, and zinc or (ii) carbon, silicon, germanium, tin, lead, titanium, zirconium, hafnium, vanadium, niobium, tantalum, chromium, molybdenum, tungsten, manganese, iron, cobalt, nickel, copper and zinc;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum $f+g$ is equal to the valence of $Y_1$ when j has a value of 0, and f and g are integers having a value such that the sum $f+g$ is equal to the valence of $Y_1$ plus $(M_3-Y_2)_j$ when j has a value other than 0.

* * * * *

UNITED STATES PATENT AND TRADEMARK OFFICE
CERTIFICATE OF CORRECTION

PATENT NO. : 5,112,789
DATED : May 12, 1992
INVENTOR(S) : James H. McCain

It is certified that error appears in the above-indentified patent and that said Letters Patent is hereby corrected as shown below:

Column 12, line 8, "$[R_1-X_1-M_1]_f-X_3-[M_3-X_4]-M_2-X_2-R_2]_g$" should read
--$[R_1-X_1-M_1]_f-X_3-[M_3-X_4]_j[M_2-X_2-R_2]g$--.

Column 16, lines 48-52, $$"Z_a - X - \underset{\underset{R_7}{|}}{\overset{\overset{R_6}{|}}{C}} - \underset{\underset{R_9}{|}}{\overset{\overset{R_8}{|}}{C}} - Y - Z_b,"$$

should read $$--Z_a - X - \underset{\underset{R_7}{|}}{\overset{\overset{R_6}{|}}{C}} - \underset{\underset{R_9}{|}}{\overset{\overset{R_8}{|}}{C}} - Y - Z'_b--$$

Column 17, line 6-8, $$"Z_a - \underset{|}{\overset{|}{X-C}} - \underset{|}{\overset{|}{C-Y}} - Z_b,"$$

should read $$--Z_a - \underset{|}{\overset{|}{X-C}} - \underset{|}{\overset{|}{C-Y}} - Z'_b--$$

Column 27, line 1, "acohols" should read --alcohols--.

Page 1 of 2

UNITED STATES PATENT AND TRADEMARK OFFICE
CERTIFICATE OF CORRECTION

PATENT NO. : 5,112,789
DATED : May 12, 1992
INVENTOR(S) : James H. McCain

It is certified that error appears in the above-indentified patent and that said Letters Patent is hereby corrected as shown below:

Claim 1, line 54, after "with" insert --an organic compound having at least one active hydrogen or--.

In the Abstract, Line 2, "IIB" should read --IIIB--.

Signed and Sealed this

Second Day of August, 1994

Attest:

BRUCE LEHMAN

Attesting Officer   Commissioner of Patents and Trademarks